US010124337B2

(12) United States Patent
Tsai et al.

(10) Patent No.: US 10,124,337 B2
(45) Date of Patent: Nov. 13, 2018

(54) APPARATUS AND METHOD FOR MICROFLUIDIC MAGNETIC SELF-ASSEMBLY AT LIQUID-LIQUID INTERFACES

(71) Applicants: Scott Tsai, Newmarket (CA); Steven Jones, Newmarket (CA); Eric Jervis, Vancouver (CA)

(72) Inventors: Scott Tsai, Newmarket (CA); Steven Jones, Newmarket (CA); Eric Jervis, Vancouver (CA)

( * ) Notice: Subject to any disclaimer, the term of this patent is extended or adjusted under 35 U.S.C. 154(b) by 2 days.

(21) Appl. No.: 15/424,048

(22) Filed: Feb. 3, 2017

(65) Prior Publication Data

US 2017/0225165 A1   Aug. 10, 2017

Related U.S. Application Data

(60) Provisional application No. 62/291,133, filed on Feb. 4, 2016.

(51) Int. Cl.
*G01N 33/553* (2006.01)
*B01L 3/00* (2006.01)
*G01N 33/543* (2006.01)

(52) U.S. Cl.
CPC ... *B01L 3/502761* (2013.01); *B01L 3/502776* (2013.01); *G01N 33/54366* (2013.01); *G01N 33/553* (2013.01); *B01L 2200/0636* (2013.01); *B01L 2200/0652* (2013.01); *B01L 2200/0668* (2013.01); *B01L 2200/0673* (2013.01); *B01L 2300/0867* (2013.01); *B01L 2400/043* (2013.01)

(58) Field of Classification Search
None
See application file for complete search history.

(56) References Cited

U.S. PATENT DOCUMENTS

| | | | | |
|---|---|---|---|---|
| 2003/0124509 A1* | 7/2003 | Kenis et al. | ............. | C12M 1/34 435/4 |
| 2004/0228205 A1* | 11/2004 | Sadler et al. | ........... | B01F 11/02 366/127 |
| 2004/0228206 A1* | 11/2004 | Sadler et al. | ........... | B01F 11/02 366/127 |

OTHER PUBLICATIONS

Albertsson, "Partition of Proteins in Liquid Polymer-Polymer Two-Phase Systems", Nature, 1958, 182(4637): 709-711.
Albertsson, et al., "Interfacial Tension of Dextran-Polyethylene Glycol-Water Two-Phase Systems", Journal of Colloid and Interface Science, 1971, 37(1): 219-222.
Atefi, et al., "Ultralow Interfacial Tensions of Aqueous Two-Phase Systems Measured Using Drop Shape", Langmuir, 2014, 30(32): 9691-9699.
Moon, et al., "Microfluidic conformal coating of non-spherical magnetic particles", Biomicrofluidics 8, 052103, (2014).
Tsai, et al., "Conformal coating of particles in microchannels by magnetic forcing", Appl. Phys. Lett. 99, 153509 (2011).

* cited by examiner

*Primary Examiner* — Christopher L Chin
(74) *Attorney, Agent, or Firm* — Bereskin & Parr LLP/S.E.N.C.R.L., s.r.l.; Tony Orsi

(57) ABSTRACT

Various embodiments are described herein for controlling the self-assembly process of paramagnetic particles and the final particle cluster size using a liquid-liquid interface. The number of paramagnetic particles within a particle cluster and coating at the liquid-liquid interface may be controlled by systematically varying the strength of an applied magnetic field gradient and the interfacial tension of the liquid-liquid interface.

26 Claims, 11 Drawing Sheets

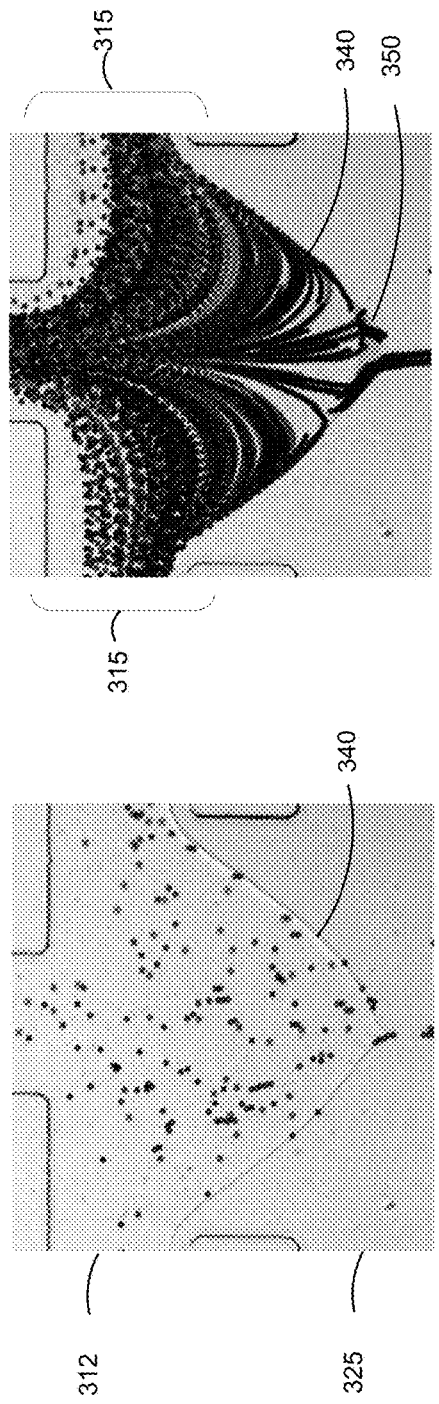
FIG. 3A
FIG. 3B
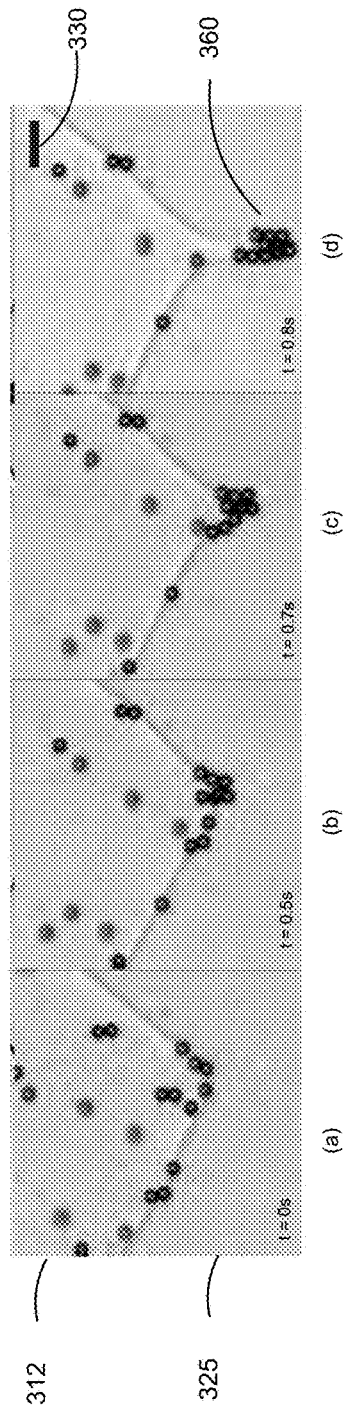
FIG. 3C

US 10,124,337 B2

APPARATUS AND METHOD FOR MICROFLUIDIC MAGNETIC SELF-ASSEMBLY AT LIQUID-LIQUID INTERFACES

CROSS-REFERENCE TO RELATED APPLICATION

This application claims the benefit of U.S. Provisional Patent Application No. 62/291,133 filed Feb. 4, 2016; the entire contents of Patent Application No. 62/291,133 are hereby incorporated by reference.

FIELD

Various embodiments are described herein for an apparatus and method that may be used to assemble particles and coat individual particles or particle clusters.

BACKGROUND

The interface formed between immiscible liquid phases has numerous applications in microfluidic devices. For example, liquid-liquid interfaces are important in separation processes and particle synthesis techniques.

Microfluidic technologies may facilitate the self-assembly of a variety of particles into particle clusters. For example, spherical particle clusters can be formed in evaporating drops, and Janus particles formed with droplet microfluidics can be designed to self-assemble into highly repeatable cluster geometries.

Particles and particle clusters may also be forced through a liquid-liquid interface, to conformally coat the particles and particle clusters in a thin film of one of two immiscible fluid phases.

SUMMARY OF VARIOUS EMBODIMENTS

In a broad aspect, at least one embodiment described herein provides a microfluidic device for processing at least one sample particle that is paramagnetic, the device comprising a cross-slot chamber including: an upper inlet portion that receives a first fluid during use, the first fluid containing the at least one sample particle; a lower inlet portion disposed below the upper inlet portion that receives a second fluid during use; third and fourth side outlet portions disposed on either of the cross-slot chamber between the upper and lower inlet portions, for providing symmetrical outlets for the first and second fluids during use; and a collection chamber for collecting the processed at least one sample particle; and a magnetic field source for providing a magnetic field that encompasses at least a portion of cross-slot chamber, wherein, during use the first fluid is introduced along a first axis into the cross-slot chamber and the second fluid is introduced along a second axis into the cross-slot chamber, the second axis being transverse to the first axis, the first and second fluids being aqueous and immiscible with respect to one another to create first and second fluid phases with a liquid-liquid interface providing an interfacial tension therebetween in the cross-slot chamber, and the magnetic field encompasses the liquid-liquid interface and is adjusted to impart a magnetic force to control movement of the at least one sample particle across the liquid-liquid interface to the cross-slot chamber.

In at least some embodiments, the liquid-liquid interface is non-linear and comprises at least one apex, and the flows of the first and second fluids produce an extensional flow field with at least one stagnation point at the at least one apex.

In at least some embodiments, the magnetic field strength is adjusted to pull the at least one particle across the liquid-liquid interface and the at least one particle is coated with a layer of liquid from the first fluid.

In at least some embodiments, at least two sample particles that are paramagnetic are brought to the liquid-liquid interface and assembled into a particle cluster due to at least one of the magnetic field and the interfacial tension.

In at least some embodiments, at least two sample particles that are paramagnetic are brought to the liquid-liquid interface and assembled into at least two sample particle chains due to at least one of the magnetic field strength and the interfacial tension.

In at least some embodiments, the magnetic field strength is adjusted to pull the at least two sample particles across the liquid-liquid interface and the at least two sample particles are coated with a layer of liquid from the first fluid.

In at least some embodiments, the at least two sample particle chains assemble into a cluster of sample particle chains before crossing the liquid-liquid interface.

In at least some embodiments, there are a plurality of paramagnetic particles and a cell having a cell membrane with at least one cell surface receptor, wherein the paramagnetic particles are functionalized to bond with the at least one cell surface receptor and processed to cross the liquid-liquid interface and be coated with a liquid layer from the first fluid.

In at least some embodiments, the magnetic field source is a permanent magnet that is aligned with the center of the liquid-liquid interface.

In at least some embodiments, the magnetic field source is an electromagnet that is aligned with the center of the liquid-liquid interface, and wherein the magnetic field is varied by varying a current through the electromagnet during use.

In at least some embodiments, the first fluid and the second fluid are both aqueous polymer mixtures and the polymers are incompatible with one another.

In at least some embodiments, the device comprises first and second fluid inlets for receiving the first fluid during use; first and second fluid microchannel networks having first and second input portions coupled to the first and second fluid inlets, respectively, the first fluid microchannel network having a first output portion being coupled to the second fluid microchannel network between the second fluid inlet and a second output portion of the second microchannel network, and the second output portion of the second microchannel network being coupled to the upper inlet portion of the cross-slot chamber; a third fluid inlet for receiving the second fluid during use; and a third microchannel network having a third input portion coupled to the third fluid inlet and a third output portion coupled to the lower inlet portion of the cross-slot chamber.

In at least some embodiments, the second output of the second microchannel network comprises a single microchannel having a first microchannel axis and the third output portion of the third microchannel comprises two microchannels with axes transverse to the first microchannel axis on either side of the lower portion of the cross-slot chamber.

In at least some embodiments, the lower inlet portion of the cross-slot chamber is wider than the upper inlet portion of the cross-slot chamber.

In another broad aspect, at least one embodiment described herein provides a method of processing at least one sample particle that is paramagnetic in a microfluidic device, the method comprising: providing a cross-slot fluid chamber for the microfluidic device; introducing the first fluid along a first axis into the cross-slot chamber and introducing the second fluid along a second axis into the cross-slot chamber, the second axis being transverse to the first axis, the first and second fluids being aqueous and immiscible with respect to one another to create first and second fluid phases with a liquid-liquid interface having an interfacial tension therebetween in the cross-slot chamber; providing a magnetic field that encompasses the liquid-liquid interface; and adjusting the magnetic field to impart a magnetic force to control movement of the at least one particle across the liquid-liquid interface to the cross-slot chamber.

In at least some embodiments, the method comprises providing the cross-slot fluid chamber with an upper inlet portion that receives the first fluid during use, the first fluid containing the at least one sample particle; a lower inlet portion disposed below the upper inlet portion that receives the second fluid during use; third and fourth side outlet portions disposed on either of the cross-slot chamber between the upper and lower inlet portions, for providing symmetrical outlets for the first and second fluids during use; and a collection chamber for collecting the processed at least one sample particle.

In at least some embodiments, the liquid-liquid interface is non-linear and comprises at least one apex, and the flows of the first and second fluids produce an extensional flow field with at least one stagnation point at the at least one apex.

In at least some embodiments, the method further comprises adjusting the magnetic field strength for pulling the at least one sample particle across the liquid-liquid interface and coating the at least one sample particle with a layer of liquid from the first fluid.

In at least some embodiments, the method further comprises bringing at least two sample particles that are paramagnetic to the liquid-liquid interface and assembling the at least two sample particles into a particle cluster due to at least one of the magnetic field strength and the interfacial tension.

In at least some embodiments, the method further comprises bringing at least two sample particles that are paramagnetic to the liquid-liquid interface and assembling the at least two sample particles into at least two particle chains due to at least one of the magnetic field strength and the interfacial tension.

In at least some embodiments, the method further comprises adjusting the magnetic field strength for pulling the at least two sample particles across the liquid-liquid interface and coating the at least two particles with a layer of liquid from the first fluid.

In at least some embodiments, the method further comprises assembling the at least two sample particle chains into a cluster of sample particle chains before crossing the liquid-liquid interface.

In at least some embodiments, there are a plurality of paramagnetic particles and a cell having a cell membrane with at least one cell surface receptor, and the method further comprises functionalizing the paramagnetic particles to bond with the at least one cell surface receptor and processing the cell and paramagnetic particles for crossing the liquid-liquid interface and being coated with a liquid layer from the first fluid.

In at least some embodiments, the magnetic field source is a permanent magnet, and the method further comprises aligning the permanent magnet with the center of the liquid-liquid interface and adjusting the distance of the permanent magnet with respect to the cross-slot chamber to provide a desired magnetic field strength.

In at least some embodiments, the magnetic field source is an electromagnet, and the method further comprises aligning the electromagnet with the center of the liquid-liquid interface, and adjusting the magnetic field by varying a current through the electromagnet during use.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 3A and 3C are photomicrographs of self-assembling microparticle clusters that occur during use of an example embodiment of a microfluidic system in accordance with the teachings herein.

FIG. 3B is a photomicrograph of microparticle trajectories that occur during use of an example embodiment of a microfluidic system in accordance with the teachings herein.

Figure 1B:
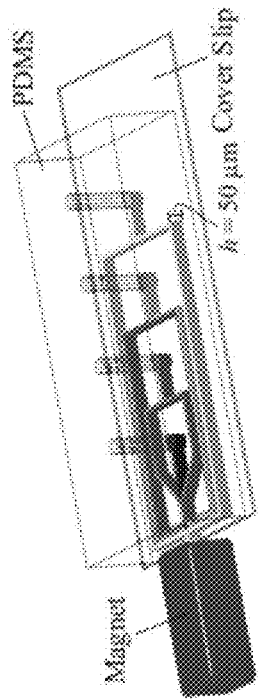
FIG. 1B is a perspective semi-transparent view of the microfluidic system of FIG. 1A.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, magnetic or fluidic connotation. For example, as used herein, the terms coupled or coupling can indicate that two elements or devices can be directly connected to one another or connected to one another through one or more intermediate elements or devices via a magnetic signal, a mechanical element, such as, conduits and the like or fluidic elements, such as a liquid interface depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "similar", "about" and "approximately" as used herein mean a reasonable amount of deviation of the modified term such that the end result is not significantly changed. These terms of degree may also be construed as including a deviation of the modified term, such as 1%, 2%, 5% or up to 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or up to 10%, for example.

Particles and particle clusters may be forced through a liquid-liquid interface, to conformally coat the particles and particle clusters in a thin film of one of the two immiscible fluid phases. For example, self-assembly and conformal coating of paramagnetic microparticle clusters may be performed in a microfluidic system by pulling the microparticles across a two-phase, co-flow, oil-water interface with an externally applied magnetic field. Depending on the application, the particle or particle clusters may be forced through the liquid-liquid interface from the water phase into the oil phase or vice versa. In general, particles may be placed initially in the phase corresponding to the material upon which a coating is to be applied. For example, if a coat of water film is desired, then the particle may be first placed in the water phase and forced to migrate into the oil phase. Conversely, to obtain an oil coating, the particles may be placed in the oil phase and forced to migrate to the water phase.

Forcing microparticles through a liquid-liquid interface via body forces such as magnetic forces may be possible when the adhesion forces between the two liquids at the interface are low (in other words, there is low interfacial tension). For oil-water systems, ultra-low interfacial tension may be achieved with the addition of surfactants. The hydrophobic and hydrophilic ends of the surfactants may align with the oil and water phases, respectively, at the interface to reduce the interfacial tension. However, use of surfactants may result in some practical limitations, such as, for example, when the concentration of surfactants is above the Critical Micelle Concentration (CMC). The CMC is the critical surfactant concentration above which additional surfactants added to the oil-water system lead to the formation of micelles in the bulk liquid phase rather than going to the liquid-liquid interface. As such, addition of more surfactants would contribute minimally to the further reduction in the interfacial tension when the system is already above the CMC.

In accordance with the teachings herein, a more suitable environment for the passage of particles through a liquid-liquid interface may be an Aqueous Two-Phase System (ATPS). Such a system may be created by dissolving two incompatible polymers in water, such that the polymers phase separate above a critical dissolved polymer concentration, without having to add surfactants. The critical dissolved polymer concentration for various common ATPS systems may be obtained from published data which may be presented as binodal curves that describe circumstances where phase-separation occurs for different liquid-liquid pairs of varying molecular weights. Alternatively, the critical dissolved polymer concentration may be determined experimentally for specific polymer combinations not generally described in published literature. The interfacial tension of an ATPS is inherently ultra-low, and this parameter may further be tuned by adjusting the dissolved polymer concentration without introduction of any surfactants. Additionally, unlike an oil phase in an oil-water system, an ATPS may be biocompatible so that self-assembly and coating systems that use an ATPS may be adapted for biological applications such as cell clustering and coating. In addition, the inherently biocompatible nature of ATPS-produced clusters may be preferable over self-assembled clusters produced in an oil-water system since the latter may require additional washing and re-suspension steps in an aqueous phase before the clusters may be used in biological or biomedical applications. Furthermore, water-water phases may permit diffusion of smaller biomolecules across the liquid interface such that the transport of nutrients may be possible. This aspect may be particularly relevant if the particles in question are cells which use regular in-flow of throughout the liquid phases to remain viable.

In accordance with the teachings herein, various embodiments are described for controlling the self-assembly process and the final particle cluster size. In particular, at least one embodiment of a system and method is described in accordance with the teachings herein for controlling the self-assembly of paramagnetic particles at a liquid-liquid interface. Specifically, the number of paramagnetic particles within a particle cluster may be controlled by systematically varying the strength of an applied magnetic field gradient and the interfacial tension of the liquid-liquid interface.

For the purposes of this disclosure, particles may refer to microparticles which may be regarded as particles whose diameters are within the micrometer scale (e.g. from 0.1 µm to 1000 µm). Such particles may be comprised of any material and may include, but not be limited to, ceramic microspheres, glass microspheres, polymer microspheres, metallic microspheres, and biological objects such as cells and islets. The particles may inherently be paramagnetic, in which they respond to the presence of a magnetic field. In some cases, particles and cells may be processed so that they are paramagnetic so as to be sensitive to magnetic fields. For example, paramagnetic microparticles may be attached to the surfaces of cells using targeted antibody-antigen interactions to make the cells paramagnetic. In other words, the surfaces of the microparticles may be functionalized with antibodies which bind to specific antigens found on the target cells' surface. The functionalized microparticles may be mixed with the cells to magnetically tag the cells.

Figure 1C:
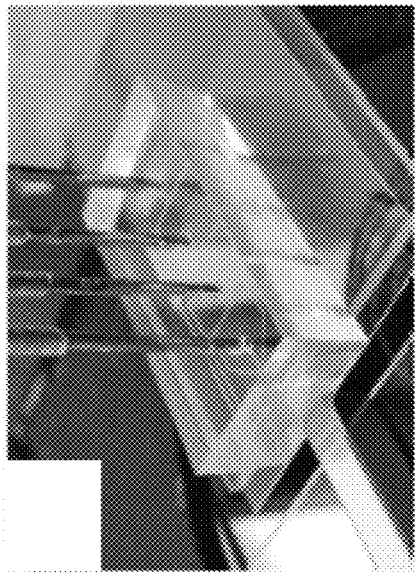
FIG. 1C is an image of an experimental setup of the microfluidic system of FIG. 1A.
Figure 1A:
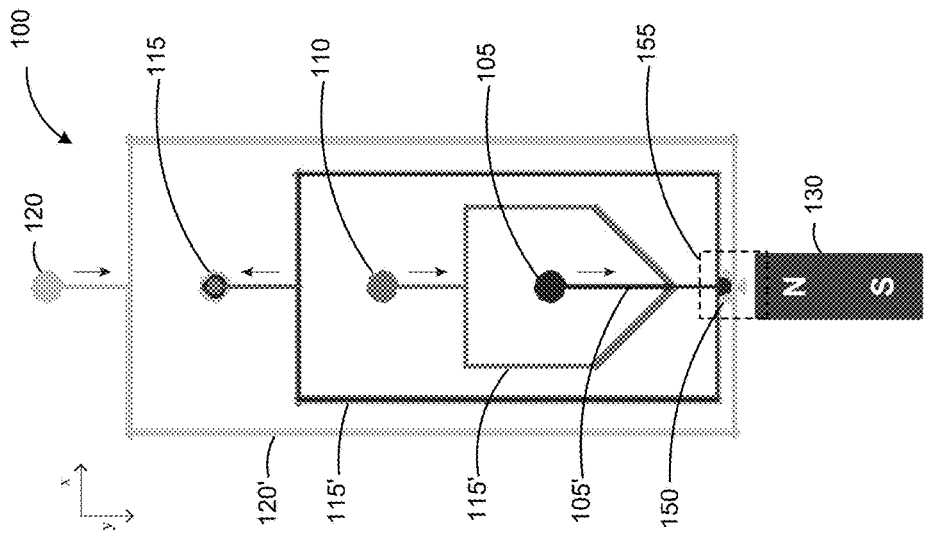
FIG. 1A is a top view of an example embodiment of a microfluidic system in accordance with the teachings herein.

Referring now to FIG. 1A, illustrated therein is the top view of an example embodiment of a microfluidic system 100 for controlling the self-assembly of paramagnetic particles in accordance with the teachings herein. Such a system may also be understood to be a lab-on-a chip, a microchannel device or a flow system. The microfluidic system 100 comprises a number of fluid inlets 105, 110, 120, an outlet 115 and a cross-slot chamber 150 that are fluidly coupled to one another using microchannels which provide for fluid flow during use. Depending on the application, the microfluidic system 100 may be scaled to accommodate the physical dimensions of the particles to be processed within the system. In some instances, the height and width of the microchannels may range from 10 µm to 500 µm. The channel lengths may range between 100 µm to 10,000 µm.

The first inlet 105 may be used to supply sample particles suspended in a first liquid for the self-assembly process. The sample particles may enter through the first inlet 105 and travel along a first fluid microchannel networking comprising microchannels 105' to the cross-slot chamber 150 in which ATPS is formed. The second inlet 110 may be used to supply the first liquid, which flows along a second fluid microchannel network comprising second microchannels 110' to the cross-slot chamber to create the first phase of the ATPS. The third inlet 120 may be used to supply the second liquid, which flows along a third fluid microchannel network comprising third microchannels 120' to the cross-slot chamber 150 to create the second phase of the ATPS. An outlet 115 may be used to collect an outflow of liquid from the microfluidic system 100 via outlet microchannels 115'. The arrows in FIG. 1A indicate the direction of fluid flow during use. A magnet 130 may be placed proximally to the cross-slot chamber 150 to apply a magnetic gradient across the cross-slot chamber 150. The sample particles introduced into the microfluidic system 100 may be paramagnetic particles that will tend to migrate in the direction of the magnet 130.

The cross-slot chamber 150 includes an upper inlet portion that receives the first fluid during use, a lower inlet portion disposed below (i.e. downstream of) the upper inlet portion that receives the second fluid during use; third and fourth side outlet portions disposed on either of the cross-slot chamber 150 between the upper and lower inlet portions, for providing symmetrical outlets for the first and second fluids during use; and a collection chamber for collecting the processed at least one particle. During use, the first fluid is introduced along a first axis into the cross-slot chamber 150 and the second fluid is introduced along a second axis into the cross-slot chamber 150, the second axis being transverse to the first axis.

The first and second fluid microchannel networks have first and second input portions that are coupled to the first and second fluid inlets, respectively. The first fluid microchannel network has a first output portion that is coupled to the second fluid microchannel network between the second fluid inlet and a second output portion of the second microchannel network. The second output portion of the second microchannel network is coupled to the upper inlet portion of the cross-slot chamber 150. The third microchannel network has a third input portion coupled to the third fluid inlet and a third output portion coupled to the lower inlet portion of the cross-slot chamber 150.

In this example embodiment, the second output of the second microchannel network comprises a single microchannel having a first microchannel axis. The third output portion of the third microchannel comprises two microchannels with axes transverse to the first microchannel axis on either side of the lower portion of the cross-slot chamber. In other embodiments, other designs may be possible as long as an extensional flow field may be set up for the first and second fluids to create a liquid-liquid interface therebetween having a desired interfacial tension and optionally, but preferably, at least one stagnation point near the liquid-liquid interface.

The magnetic force exerted on a given sample particle to pull the particle along the cross-slot chamber 150 may be proportional to the particle's volume (i.e. related to the particle's radius to the power of three). As such, smaller sample particles may experience weaker magnetic forces. The decrease in magnetic force with decreasing size may happen more quickly than the rate of decrease of the interfacial tension force with particle size, because the interfacial tension force decreases with the circumference of the particle (i.e. related to the particle's radius to the power of one). Therefore, generally, it may be much more difficult to control nanoparticles than it is for microparticles. While a stronger magnetic field may be applied for smaller particles, generally every paramagnetic material has a saturation magnetization that may not be exceeded, which means that the magnetic force exerted on a small particle such as a nanoparticle may reach a maximum. Once magnetic saturation is reached (i.e. all of the material's magnetic dipoles are aligned with the externally applied magnetic field) it may not be possible to further enhance the magnetization of that material. As a result, at some point, increasing the magnetic field strength may not produce a stronger magnetic force to pull a nanoparticle across the liquid-liquid phase.

It should be noted that while a permanent magnet 130 is depicted in FIG. 1A, any device capable of producing a magnetic field gradient may be used. For example, in some embodiments, an electromagnet may be used instead of a permanent magnet. The magnetic field strength generated by the electromagnet may be varied by adjusting the magnitude of the current supplied to the electromagnet, which is advantageous as the strength of the magnetic field may be changed during use without having to make cumbersome physical modifications to the microfluidic system 100.

The microfluidic system 100 may be implemented by fabricating a microfluidic chip using a variety of materials such as, but not limited to, Poly(methyl methacrylate) (PMMA) or a 3D printed material including acrylic or other plastics. In the present example embodiment, poly-dimethylsiloxane (PDMS, Sylgard 184, Dow Corning, Midland, Mich., USA) may be used. The microchannels may be fabricated in a PDMS layer using standard soft lithography techniques. Geometries for the microchannels may be specified via computer-aided design (CAD) software to produce a high-resolution mask (e.g. at 25,000 dpi resolution, CAD/ART Services Inc., Bandon, Oreg., USA) to form a photomask for the lithography process. An SU-8 2025 negative photoresist (Microchem., Newton, Mass.) may then be spin-coated onto a 4-inch silicon wafer substrate and exposed to UV light through the photomask. After the silicon wafer is developed, the PDMS channels are formed by pouring PDMS (10:1 prepolymer to curing agent) over the silicon wafer, which is then cured in an oven, to produce microchannels with a height h=50 μm. The edge of the patterned PDMS layer may then be trimmed with a straight razor (Personna, Verona, Va., USA) to allow the placement of a permanent magnet in close proximity (<1 mm) to the cross-slot region of the microchannel. Inlet and outlet holes may then be punched into the patterned PDMS layer with a 1 mm diameter biopsy punch (Integra Miltex. Inc., Rietheim-Weilheim, Germany). The patterned PDMS layer may then be permanently bonded via application of an oxygen plasma treatment (Harrick Plasma, Ithaca, N.Y., USA) to a glass cover slip (50×22×0.2 mm; Thermo Fisher Scientific Inc., MA, USA) with the crossflow region of the PDMS layer placed at the outside edge of the glass slide (see FIGS. 1B and 1C). FIG. 1B shows the patterned layer of PDMS that is plasma-bonded to a glass cover slip with a permanent magnet placed at the edge of the microfluidic chip to provide the magnetic field. FIG. 1C shows an experimental set-up of the microfluidic system 100 with attached inlet and outlet ports. The microfluidic chip and permanent magnet are aligned on a 3D printed fixture (not shown), where the face of the magnet is centered on the cross-slot region.

In some embodiments, the first liquid may be an aqueous solution of Dextran (DEX), and the second liquid may be aqueous PolyEthylene Glycol (PEG) solution. Therefore, the ATPS liquid-liquid interface may be formed in an extensional flow between converging flows of the PEG and DEX within the cross-slot chamber 150. Table 1 lists example polymer concentrations and fluid properties of eight DEX-PEG fluid combinations and the resultant interfacial tension. In Table 1, the parameters $\eta_p$ and $\eta_d$ correspond to the viscosities of PEG and DEX, respectively, and γ is the interfacial tension at the PEG-DEX interface.

It should be understood that many other aqueous polymer pairs may be used in alternative embodiments. Specifically, any two polymer pairs may be used if they are miscible in water, but incompatible with each other, so that they will phase-separate above some threshold concentration in water.

Therefore, in some embodiments, the interfacial tension may be used as a design parameter and certain liquids having certain concentrations of polymers and certain viscosities may be selected to achieve a desired amount of interfacial tension.

TABLE 1

| ATPS | PEG % (w/v) | DEX % (w/v) | $\eta_p$ (mPa · s) | $\eta_d$ (mPa · s) | γ (mN/m) |
|---|---|---|---|---|---|
| 1 | 5.0 | 6.4 | 5.1 | 14.7 | 0.012 |
| 2 | 5.0 | 16.0 | 9.8 | 32.3 | 0.037 |
| 3 | 5.0 | 20.0 | 12.6 | 50.2 | 0.042 |
| 4 | 10.0 | 12.8 | 15.0 | 65.1 | 0.082 |
| 5 | 10.0 | 16.0 | 16.4 | 67.5 | 0.103 |
| 6 | 10.0 | 20.0 | 28.0 | 153.3 | 0.150 |
| 7 | 15.0 | 19.2 | 39.1 | 248.7 | 0.209 |
| 8 | 20.0 | 25.6 | 89.3 | 713.9 | 0.381 |

The particles and the two aqueous fluids may be introduced into the microfluidic system 100 via syringes, operated by syringe pumps, for example, coupled through polyethylene tubing to the corresponding inlets. The syringes may be coupled to the tubing via blunt needle syringe tips, for example. The syringe pumps may be provided by Harvard Apparatus (Holliston, Mass., USA), the polyethylene tubing may be provided by Instech Laboratories, Inc. (PA, USA), and the blunt needle syringe tips may be provided by Fishman Corporation (MA, USA). The syringe pump that controls the flow rate of the suspended particles may be positioned vertically above the microfluidic chip. This configuration may reduce variations in particle flux into the microfluidic system 100 from settling particles if the syringe was not vertically positioned. Additionally, in at least some cases, the particle suspension may be remixed just prior to injection into the microfluidic device 100 to ensure a homogeneous mixture. In a typical timescale for a set of experiments (about 30 min.), a significant variation in the particle flux coming into the microchannel was not observed.

Cells may be introduced to the microfluidic system 100 in the same manner. Specifically, the cells and functionalized paramagnetic particles described above may be mixed with the DEX solution and flowed through the microfluidic device 100 to coat the cells with the second fluid.

Figure 2:
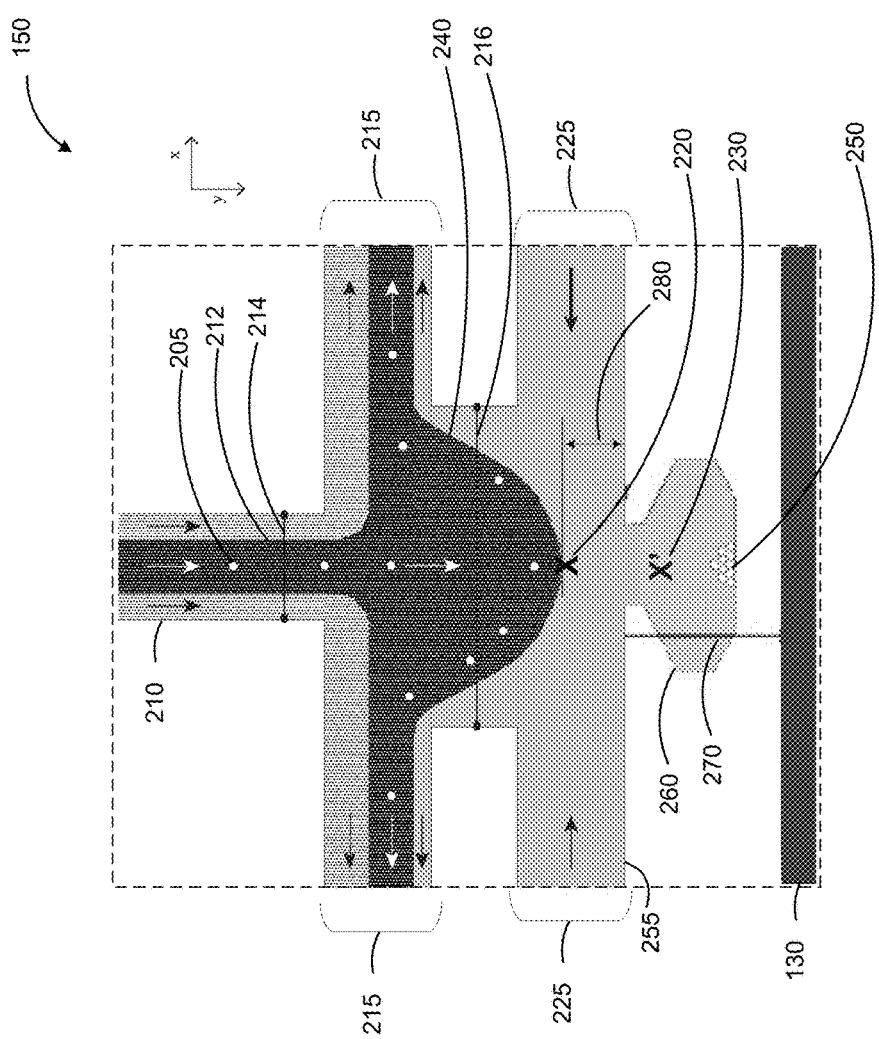
FIG. 2 is a schematic diagram of an example embodiment of a cross-slot chamber that may be used in the microfluidic system of FIG. 1A in accordance with the teachings herein.

Referring now to FIG. 2, shown therein is a schematic diagram of an example embodiment of the cross-slot chamber 150. The area depicted corresponds to the area bounded by the dotted box 150 of FIG. 1A. Similar to FIG. 1A, arrows in the diagram indicate the direction of fluid flow during use. In this example embodiment, a longitudinal axis may be defined in which the feed flow of the first liquid 210 runs parallel to the sides of microchannels 105'. The feed flow of the second liquid 255 may then be said to flow parallel to microchannels 115' but along a transverse direction with respect to the feed flow of the first liquid and flowing toward either side of the longitudinal axis of the microchannels 105' carrying the first liquid 210. Microchannels 105' for the first liquid 205 have a first channel width 214 that may be narrower than a second channel width 216 of the microchannels 115' for the second liquid 255 to provide an asymmetrical geometry for the cross-slot chamber 150. For example, in some embodiments the first microchannel width 214 may be 250 μm, and the second microchannel width 216 may be 750 μm. The asymmetrical cross-slot chamber geometry along the longitudinal axis of the first liquid flow 210 may allow for a curved liquid-liquid interface and extensional flows that create a hydrodynamic trap, due to one or more stagnation points that are formed in areas when the Reynolds number is small. Extensional flows may be used to reduce the speed of a particle 205 as it arrives at the liquid-liquid interface 240. During equilibrium, the first liquid 210 forms a first liquid phase on one side of the ATPS 240 and the second liquid 255 forms a second liquid phase on an opposing side of the ATPS 240 to the first liquid phase. While one particle 205 is referred to for ease of illustration it should be understood that there can be many particles 205 in the first liquid 210.

In some embodiments, other geometries may be used to generate the liquid-liquid interface and pull sample particles across such an interface. For example, two types of incompatible aqueous fluids may co-flow within a straight fluid channel thereby forming an interface as they flow along the channel. A magnet may be embedded adjacent to the channel to pull and aggregate sample particles at the interface. However, this design may not result in efficient particle clustering as there may not be a stagnation point where the flow velocity is negligible or zero.

Alternatively, in some embodiments, a circular channel design with a desk-shaped magnet in the middle of the circle may also be used. Again, in this configuration, the two aqueous fluids co-flow in the circular channel. Sample particles from the fluid stream farther from the magnet are pulled towards the adjacent stream, and self-assemble at the interface between the two streams. However, similarly to the straight channel configuration, this configuration may not result in efficient particle clustering as there may not be a stagnation point where the flow velocity is negligible or zero.

In some embodiments, the ATPS can be prepared by combining aqueous solutions of PEG (Mw 35 k, Sigma-Aldrich, St. Louis, Mo., USA) and DEX (Mw 500 k, Pharmacosmos, Holbaek, Denmark). The preparation procedure may be based on the methodology of Atefi et al. (E. Atefi, J. A. Mann Jr and H. Tavana, Langmuir, 2014, 30, 9691-9699.). For example, for each ATPS, a pair of 100 mL stock solutions of PEG and DEX may be prepared, where the stock solutions consist of 5.0-20.0% (w/v) PEG and 6.4-25.6% (w/v) DEX, dissolved in deionized (DI) water. Each pair of PEG and DEX stock solutions may be combined, vigorously mixed, and left for >24 hours to completely separate. The high-density DEX-rich phase may then be separated from the low-density PEG-rich phase with syringes (BD Medical, Franklin Lakes, N.J., USA). A glass viscometer may be used to measure the DEX and PEG phase viscosities, $n_d$ and $n_p$, respectively, and the values of interfacial tension reported by Atefi et al. may be used.

In some embodiments the particle 205 may be a polystyrene-based paramagnetic microparticle with radius a=5 μm. In the present example embodiment, the particles are suspended in a DEX phase and introduced into DEX-PEG ATPS. For example, the microparticles may be prepared by adding a stock microparticle solution (5% solid concentration) to a volume (e.g. 1 mL) of DEX, and thoroughly mixed with a vortex mixer. The particle suspension may then be flash centrifuged in a conical vial, and a carrier liquid may be removed with a pipette. The washed microparticle pellet is then re-suspended in a volume (e.g. 1 mL) of DEX, and later injected into the microfluidic system 100 at the first inlet 105 during use.

The flow of particles 205 may be flow-focused by the first fluid phase sheath flow 210 (shown in a light shade in FIG. 2). The phase sheath flow 210 may be produced by introducing the DEX solution into the second inlet 110 of the microfluidic system 100. The focused flow may direct the particles 205 to the center of the microchannel 105' and enhance clustering efficiency at the DEX-PEG liquid-liquid interface 240 (explained in further detail below). The flow-focused first liquid phase 212 (e.g. DEX phase) may converge with the second liquid phase 225 (e.g. PEG phase) in the cross-slot chamber 150 such that the liquid-liquid interface 240 is stable. The second liquid 225 and the first liquid 210 may flow into symmetrical channels 215 in an extensional flow to one or more outlets.

Under such flow conditions, the cross-slot microchannel geometry may produce an extensional flow field having a stagnation point in the center region of the symmetrical converging flows. For example, stagnation points may be formed at the apex 220 of the liquid-liquid interface 240 (denoted by X), and at the throat 230 of the collection chamber 260 in the second liquid phase 225 (denoted by X'). The stagnation point X at the apex 220 of the liquid-liquid interface 240 may be used to reduce the speed of the fluid flowing into the apex 220, which in turn may advantageously reduce the drag force experienced by the particles 205 during the self-assembly process. The character of the extensional flow may also bring particles directly to the liquid-liquid interface 240, which may provide advantages over known co-flow self-assembly systems in which the particles must generally be magnetically forced through a bulk fluid phase to reach the fluid-fluid interface. Accordingly, the microchannel geometries of the fluid microchannels and the cross-slot chamber 150 may be fabricated to facilitate or enhance the co-flow in the cross-slot chamber 150 of the two liquids such as, but not limited to DEX and PEG, for example, so that they meet at the junction to form a curved liquid-liquid interface 140 as in FIG. 2.

Formation of the curved liquid-liquid interface 140 may be used to drive the self-assembly process towards the apex 220 of the curved interface 140. As a result, larger particle clusters may be produced as compared to known co-flow self-assembly microchannels. Furthermore, self-assembled clusters, such as cluster 250, may be held in the collection chamber 260 as a result of the magnetic field applied to the area by the magnet 130. In some embodiments, the particles may be subsequently released from the collection chamber 260 by de-magnetizing (i.e. removal of the magnetic field) for collection at a side outlet (not shown).

In some embodiments, a curved liquid-liquid interface may be formed by the co-laminar flow of two fluids next to each other, in the absence of a stagnation point or extensional flow. Here, particles may be pulled from the first liquid phase to the second liquid phase. However, in such geometries, the particles may not be able to slow down because there are no stagnation points and, as a result, the efficiency with respect to particle aggregation and assembly of clusters of particles as well as potentially coating of particle clusters (described in detail below) may be lowered."

In the example embodiment, the magnet 130 may be a permanent magnet. For example, the magnet 130 may be a neodymium iron boron magnet (NdFeB, B22X0, K. J. Magnetics, Jamison, Pa., USA) with magnetization M~1.05 MA/m. The magnet 130 may be placed in close proximity to the cross-junction 150 of the microfluidic system 100. The magnet 130 may be secured in a structure, such as the glass slide, to permit repeatable alignment and placement of the magnet at a desired magnetization distance 270, denoted as $l_m$. In some embodiments, the magnet 130 may be positioned such that the center of the magnet face is aligned with the microfluidic cross-slot region 150 to reduce the vertical and lateral components of the magnetic field gradient.

In some embodiments, the flow rates of the particle suspension and the phase sheath flow of the first liquid may be matched. For example, they may each be set to a flow rate of 2 μL/min, for a total flow rate $Q_d=4$ μL/min while the phase flow rate of the second liquid may initially be set to $Q_p=2$ μL/min. The difference in viscosity ratios between the first and second liquid phases for different ATPS compositions may require small adjustments in the second liquid flow rate (e.g. setting $Q_p$ between 1.8-4.4 μL/min) to maintain a desired apex distance 280 (e.g. 150 μm) between the apex 220 of the liquid-liquid interface 240 and the second liquid channel wall 255.

Most of the experimental images shown herein are captured using an inverted microscope (IX71, Olympus Corp., Tokyo, Japan) with a 20× objective, and an attached high speed camera (Miro M110, Vision Research, Wayne, N.J., USA) operating at a frame rate of 100 fps, and an exposure time of 1,000 μs. High resolution images are taken with a 50× objective, at a frame rate of 200 fps, and an exposure time of 500 μs. The program ImageJ was used for image processing.

The self-assembling nature of the particles at the apex 220 of the ATPS liquid-liquid interface 240 formed by the extensional flow may be attributable to the local magnetic field gradient provided by the magnet 130. As shown in FIG. 3A, with the magnetic field from the magnet present, if the self-assembled particle cluster is sufficiently large to overcome opposing forces (e.g. viscous forces such as drag and the restoring forces due to the interfacial tension of the liquid-liquid interface), it may pass through the liquid-liquid interface 340 from the first liquid phase 312 into the second liquid phase 325. FIG. 3B shows the possible trajectories of microparticles as they flow through the cross-slot chamber 150 in the presence of a magnetic field. Particles at the center of the first liquid phase 312 may flow directly to the apex 350 of the liquid-liquid interface 340, where the particles may be able to self-assemble into a cluster. Particles that are farther from the center of the channel when they enter into the cross-slot chamber 150 may be deflected away from the centerline by the bulk fluid flow, but may be able to still reach the liquid-liquid interface 340. The particles that reach the interface farther away from the stagnation point (i.e. farther from the apex 350) may eventually flow with the bulk fluid to one of the symmetrical side outlets 315.

Referring now to FIG. 3C, panels a to d show a time lapse view of the self-assembly of a microparticle cluster at the liquid-liquid interface which then subsequently traverses from the first liquid phase 312 (e.g. DEX phase) into the second liquid phase 325 (e.g. PEG phase) as a cluster. Time indices are shown at the bottom left corner of each panel. In this example a cluster with nine particles, may be produced. This particle cluster may be denoted by a particle number, N, and for this example N=9.

Figure 4A:
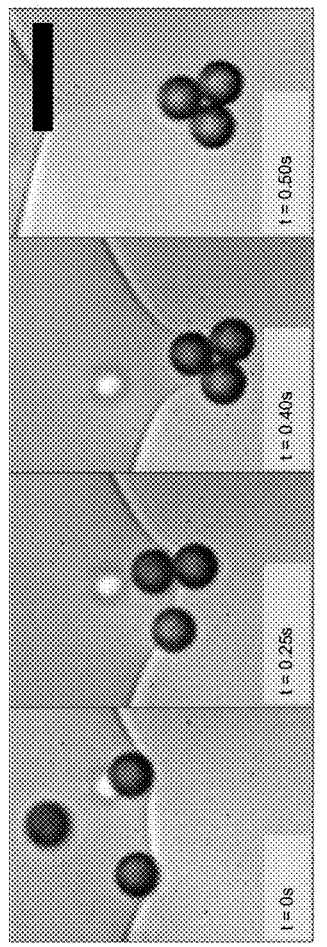
FIGS. 4A-4C are time-elapsed photomicrographs of self-assembly of microparticle clusters and particle chains during use of an example embodiment of a microfluidic system in accordance with the teachings herein.
Figure 4B:
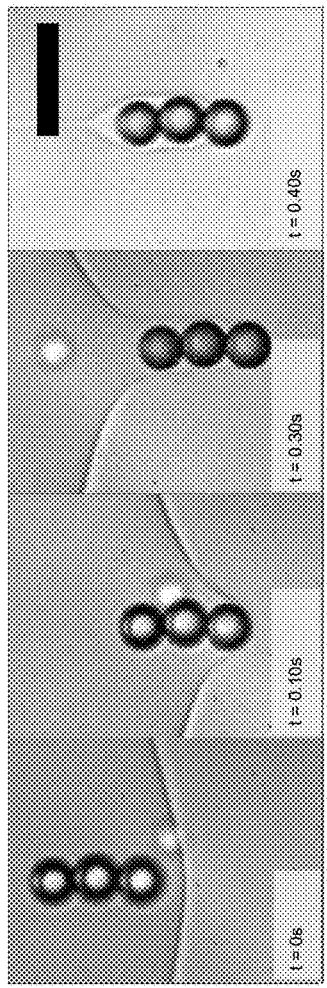
Figure 4C:
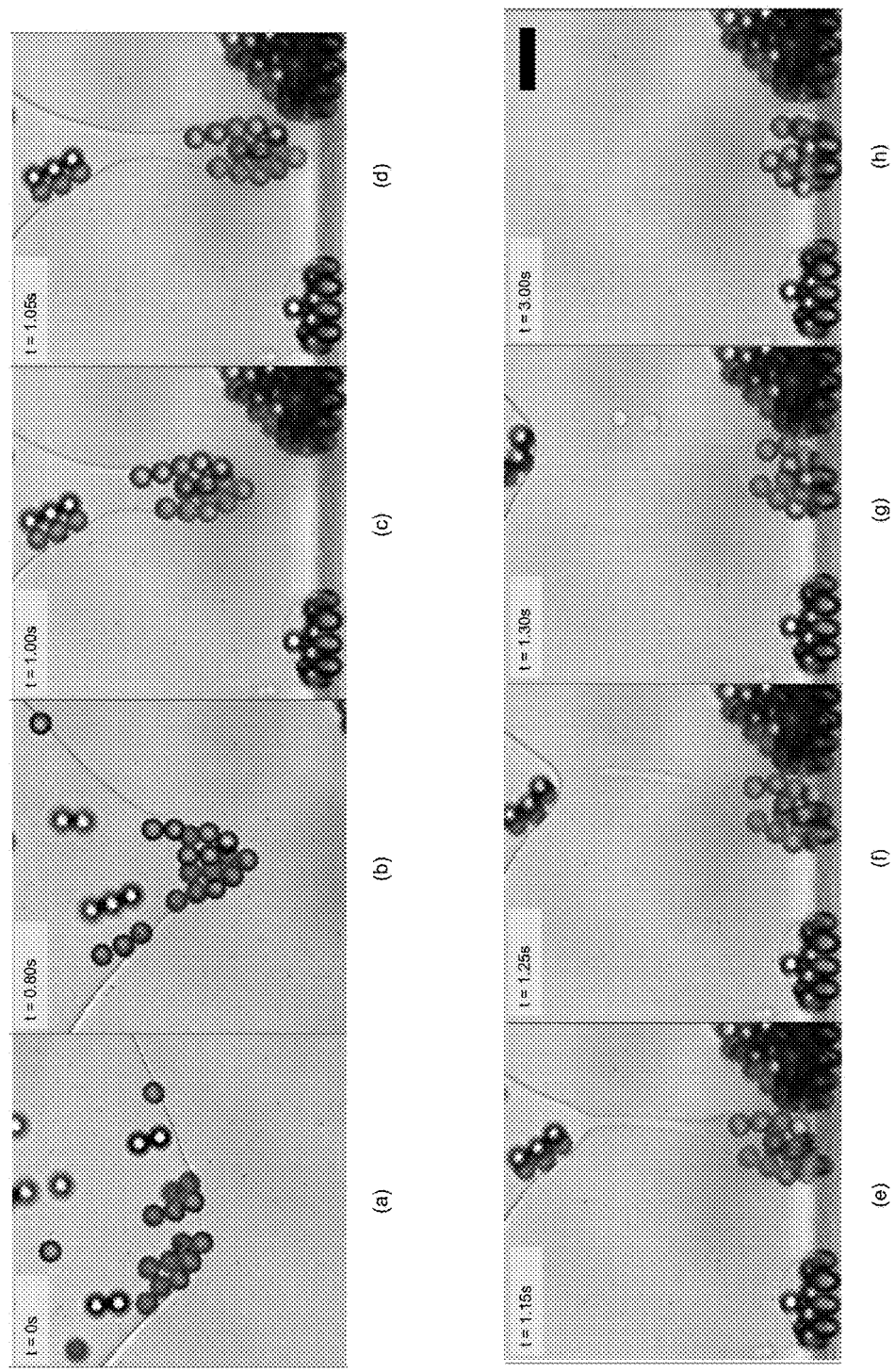

In some embodiments, the combination of the interfacial effects of the presence of the liquid-liquid interface, influence of the magnetic field, and hydrodynamic forces generated by the extensional flow field may influence the self-assembly process of the particles. More specifically, two types of particle self-assembly may be observed, in which the particle behavior may be categorized as "interfacial self-assembly" or "magnetic self-assembly". FIGS. 4A-4C show time-lapse photomicrographs of these two types of self-assembly. During interfacial self-assembly, individual paramagnetic particles as shown in FIG. 4A and particle chains as shown in FIG. 4C may self-assemble at the liquid-liquid interface. When the particle clusters reach beyond a critical size to overcome the opposing forces at the interface, they pass through the interface. In magnetic self-assembly, paramagnetic particle chains may be assembled upstream of the liquid-liquid interface and may pass through the liquid-liquid interface without further interaction with other particles at the interface as shown in FIG. 4B. In other words, prior to arrival at the liquid-liquid interface, the paramagnetic particles have been assembled by magnetism alone. When these assembled particles arrive at the interface, they are already above the critical size needed to pass through the interface.

In some embodiments it may be observed that within regions of the cross-slot chamber under influence of the magnetic field, paramagnetic particles in close proximity to each other (e.g. within a distance of approximately one particle radius of one another) may be able to align into chains as a result of magnetic dipole-dipole interactions. This behavior may be observed more frequently with two individual particles aligning into a doublet. However, particle chains with a greater number of particles may also form. The formation of particle chains may occur more frequently as particles enter the cross-slot chamber, due to the increased strength of the magnetic field as the particles flow closer to the magnet 130.

In some embodiments, a higher interfacial tension γ may be present so that smaller particle chains, such as doublets, may not be able to pass through the interface since these pre-assembled particles do not have sufficient magnetic force (e.g. because they are not large enough) to pass through the interface directly. Instead, these particle chains interact with other particles at the liquid-liquid interface, to form larger clusters before becoming large enough to pass through the interface as shown in FIG. 3C. In other embodiments, if the liquid-liquid interfacial tension γ is sufficiently low, particle chains may be formed upstream of the interface and may be able to pass directly though the interface without any other interactions at the interface as shown in FIG. 3B.

As a result of the influences of the strength of the applied magnetic field at various positions of the cross-slot chamber 150 and the degree of interfacial tension, some of the self-assembled particles may be assembled under magnetic self-assembly while other self-assembled particles may be assembled under interfacial self-assembly. The type of assembly undertaken by the particles may be dependent on the ratio of the magnetic field strength to the interfacial tension or, similarly, on the ratio of magnetic field strength to the liquid viscosity, since lower viscosity may reduce interfacial tension and vice versa. In some embodiments, where the ratio is large (e.g. magnetic field strength>>interfacial tension), it may be more likely for particles to assemble before arriving at the liquid-liquid interface and pass through as they reach the interface. In some embodiments, where the interfacial tension may be greater than the magnetic force acting on a single paramagnetic particle, particle clusters may be formed via interfacial self-assembly because a single particle may not be able to pass through the interface, while a larger cluster of particles may achieve the critical size needed to pass through the liquid-liquid interface. This condition may suggest that the liquid-liquid interface of the ATPS may be more influential with respect to determining the size of the resultant self-assembled particle clusters. In some embodiments, the interfacial tension may be reduced such that the proportion of particle clusters that are produced by magnetic self-assembly may increase. In other embodiments, the magnetic field strength may be adjusted by moving the magnet closer to or further away from the cross-slot chamber to adjust the ratio between magnetic field and interfacial tension to alter the ratio of magnetic particle clusters self-assembling at the interface to the pre-assembled particle clusters. In yet other embodiments, magnetic particle chains that form upstream of the liquid-liquid interface may also self-assemble with other particles as they arrive at the liquid-liquid interface.

Figure 5:
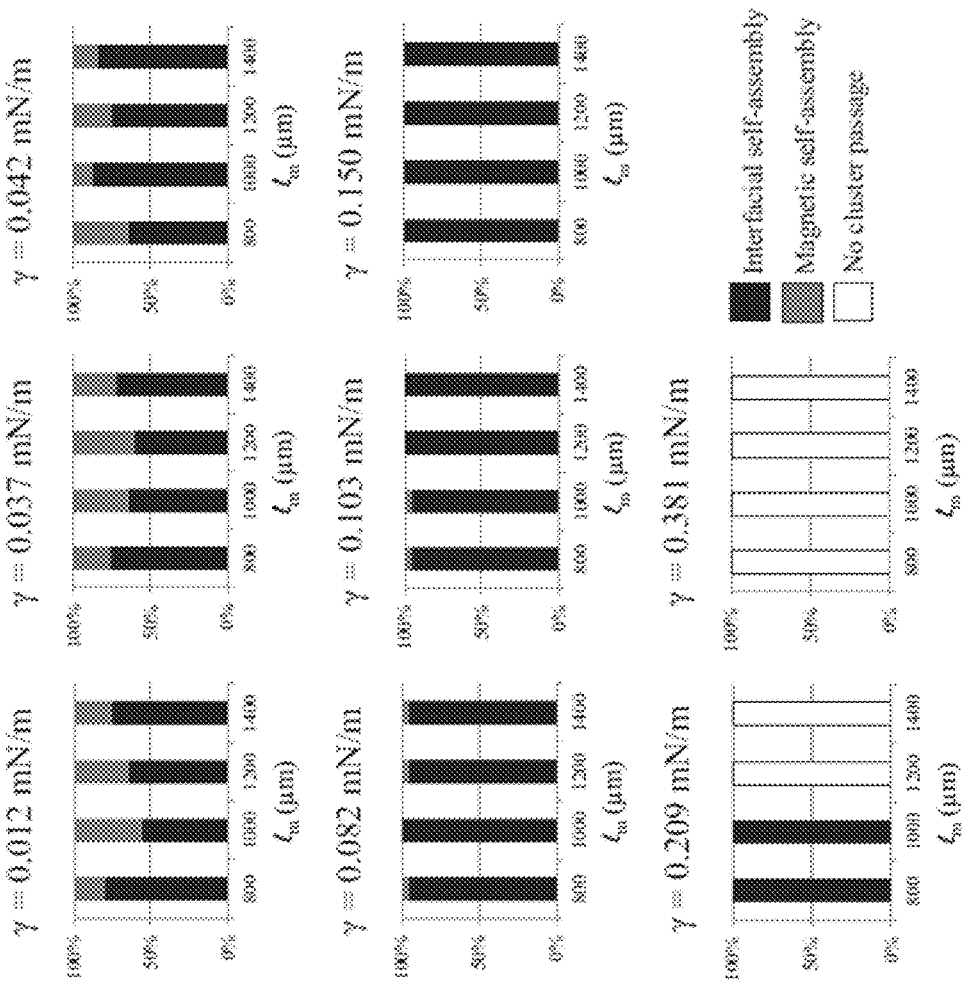
FIG. 5 includes a series of stacked bar charts showing the percentage of each self-assembly type, versus magnet distance in the microfluidic system of FIG. 1A.

FIG. 5 includes stacked bar graphs showing the percentage of each self-assembly type, versus magnet distance $l_m$. Interfacial self-assembly and magnetic self-assembly are indicated by black and gray bars, respectively, and white bars show instances where none of the self-assembled clusters were able to pass through the interface. The results from each set of magnet distance $l_m$ and interfacial tension $\gamma$ are from the first 25 clusters that pass through the liquid-liquid interface as seen in the experimental videos that were recorded.

In some embodiments, the size of the self-assembled particle clusters that are able to cross the ATPS liquid-liquid interface may be controlled. For example, the number of particles N within an individual cluster, may be controlled by systematically varying the location of the magnet from the cross-slot region 150, as expressed as the distance $l_m$ (i.e. the magnetization distance 270 of FIG. 2), by keeping the distance $l_m$ constant and adjusting the magnetic field strength (e.g. by using an electromagnet and varying its current) or by adjusting the liquid-liquid interfacial tension $\gamma$. In some embodiments, it may be desirable to dynamically control the particle size during mid-use of the microfluidic system 100 (i.e. controlling N "on the fly") by adjusting the magnetic field strength. While interfacial tension may be varied, it may be impractical to do so during use of the microfluidic system 100. However, varying the magnetic field strength and the magnetic field gradient may be accomplished by repositioning the magnet to the desired magnetization distance $l_m$ or by using an electromagnet and varying its current.

Figure 6:
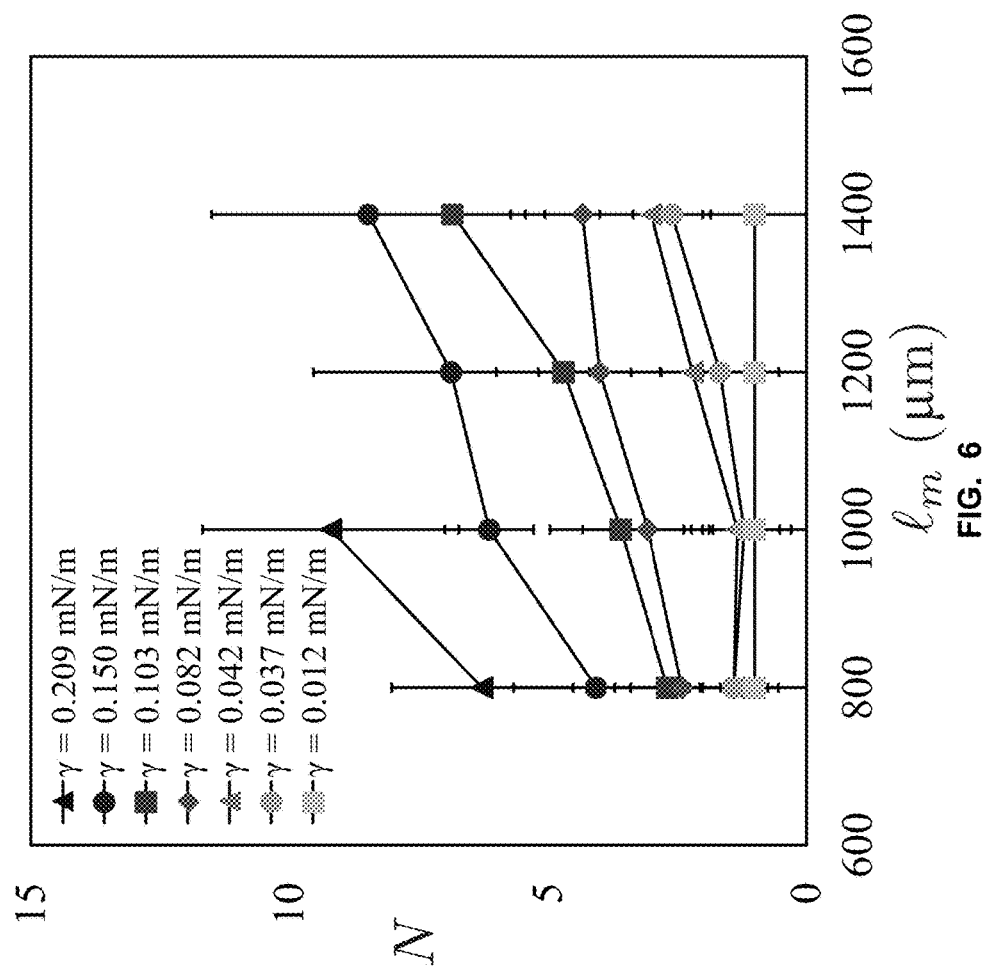
FIG. 6 is a plot of particle cluster number as a function of magnet distance for an example embodiment of a microfluidic system in accordance with the teachings herein.

Referring now to FIG. 6, shown therein is a representative plot of the cluster particle number N as a function of the magnet distance $l_m$ for an example embodiment of a microfluidic system in accordance with the teachings herein. In general, an increase in magnetic distance $l_m$ may reduce the strength of the magnetic field. As a result, a greater number of particles may be required to cluster together to overcome the interfacial tension energy barrier in order to traverse the interface. Additionally, modification of the interfacial tension $\gamma$ of the liquid-liquid interface by adjusting the ATPS polymer concentrations (e.g. those listed in Table 1) may also affect the particle cluster size, since with greater interfacial tension more energy may be needed to traverse the interface. As such, a monotonic increase in N with increasing magnetization distance $l_m$ and/or with increasing interfacial tension $\gamma$ may be observed.

At the liquid-liquid interface, the competition between the magnetic force $F_m$ and the interfacial tension restoring force $F_\gamma$ may determine whether a particle or cluster of particles can pass through the interface. The force balance at equilibrium in the direction normal to the ATPS interface at the apex 220 may be approximated according to equation 1:

$$F_m \approx F_\gamma \qquad (1)$$

For N particles, the magnetic force $F_m$ may be determined according to equation 2:

$$F_m = 4\pi N a^3 \mu_0 \frac{\chi}{\chi+3} \frac{\partial H^2}{\partial y} \qquad (2)$$

where $\mu_0 = 1.257 \times 10^{-6}$ m kg s$^{-2}$ A$^{-2}$ is the permeability of free space, and $\chi$ is the magnetic susceptibility of the magnetic particles. For example, in some embodiments, $\chi \approx O(10^{-3})$. The variable H denotes the magnetic field. The interfacial tension restoring force $F_\gamma$ may have a magnitude according to $F_\gamma \approx 2\pi\gamma l_c$, where the particle cluster characteristic length may be defined by $l_c^3 \approx N a^3$ or $l_c \approx N^{1/3}$.

Non-dimensionalizing via $H = M\hat{H}$ and $y = l_m \hat{y}$, and recognizing that since $\chi \ll 1$, so that $$\frac{\chi}{\chi+3} \to O(\chi),$$

equation 1 may be rearranged to equation 3:

$$2N^{2/3} Bo_m \frac{\partial \hat{H}^2}{\partial \hat{y}} - 1 = 0 \qquad (3)$$

where the magnetic Bond number $Bo_m$ is given by equation 4.

$$Bo_m = \frac{a^2 M^2 \chi \mu_o}{\ell_m \gamma} \qquad (4)$$

The magnetic Bond number is an indication of the ratio of cell magnetic force to ATPS interfacial tension.

Therefore, a change in the type of polymer used or a change in polymer concentration may change the interfacial tension which also changes the magnetic Bond number. In essence, the magnetic Bond number takes into consideration the effects of altering the material or concentration of material used to create the liquid-liquid interface. For example, if the PEG concentration in a PEG-DEX pair is reduced, the interfacial tension may be reduced. Lowering the interfacial tension raises the magnetic Bond number since interfacial tension appears in the denominator, which may play a role in determining whether or not a particle or a cluster of particles becomes coated, as described in more detail below.

The choice of non-dimensionalization results in $$\frac{\partial \hat{H}^2}{\partial \hat{y}} = O \qquad (1)$$

assuming that the magnetic field H varies by approximately the amount M across the distance $l_m$. Therefore, the number of particles N may expressed according to equation 5:

$$N = \kappa Bo_m^{-3/2} \qquad (5)$$

where $\kappa$ is a constant prefactor that reflects the environmental conditions of the system that may be held constant (e.g. temperature). This constant prefactor may be determined experimentally by examining the relationship between N and $Bo_m$ and deriving a constant of proportionality from that relationship using an appropriate data-fit. Equation 5 also suggests that the number of particles N within a cluster scales with a power law of the magnetic Bond number. Based on the above relations, for example, a desired magnetization distance may be determined for a desired particle cluster size N and a given interfacial tension for a particular ATPS.

Figure 7:
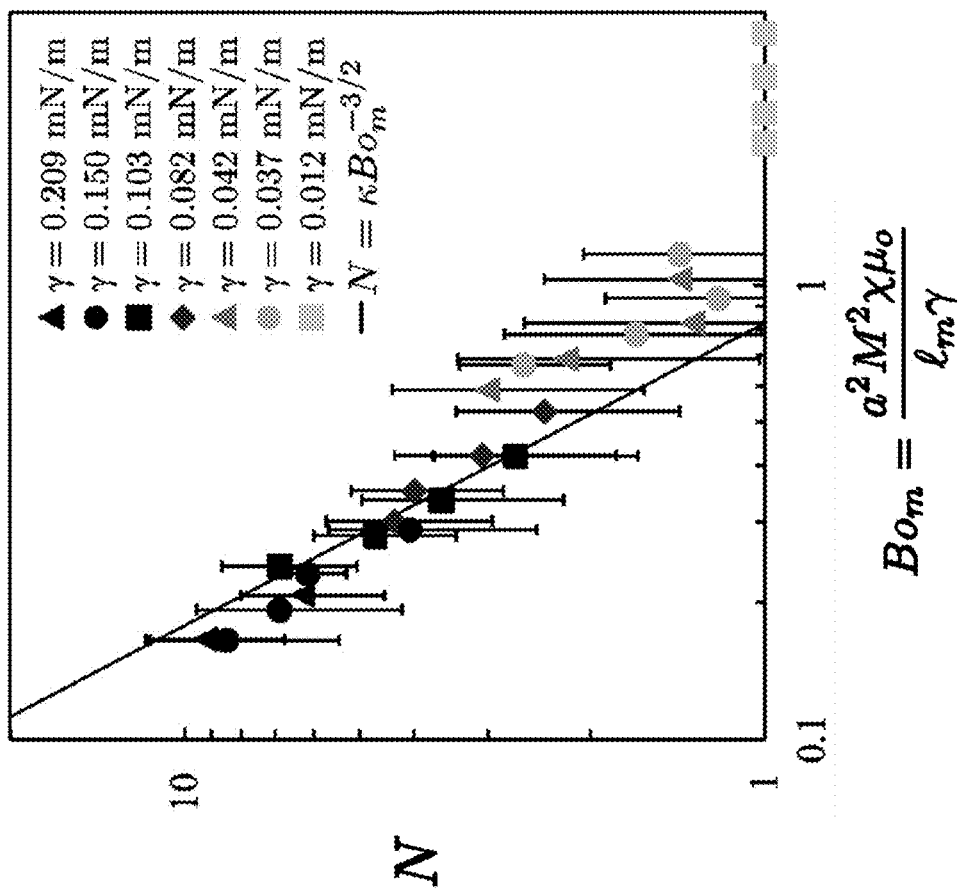
FIG. 7 is a plot of particle cluster number as a function of magnetic Bond number for an example embodiment of a microfluidic system in accordance with the teachings herein.

Referring now to FIG. 7, shown therein is a log-log plot of theoretical and measured values of particle cluster number N as a function of magnetic Bond number $Bo_m$ for various interfacial tensions for an example embodiment of a microfluidic system in accordance with the teachings herein in which $\kappa \approx 0.75$. As shown, the number of particles N within a particle cluster may decrease with increasing magnetic Bond number. However, when the magnetic Bond number is increased, a smaller cluster size N may be obtained in the model compared to actual measured values. Such an observation may be due to the tendency of particles located in the region of influence of a strong magnetic field, which may correspond to a large value of $Bo_m$, to align into particle chains via strong dipole-dipole interactions. Also, the particle chain cluster geometry may lead to the characteristic length $l_c \rightarrow \alpha$, in which case equation 1 may then reduce to $N \propto Bo_m^{-1}$. This effect of actual measured values of N deviating from the model may occur where the interfacial tension $\gamma$ is low, which generally corresponds to lower fluid viscosities $\eta_d$ and $\eta_p$ (see e.g. Table 1). The lower viscosities may allow the particles to reorient into particle chains more readily resulting from a lower drag force, which may also contribute to final particle cluster sizes that may be larger than the cluster particle size N determined by the model.

Figure 8A:
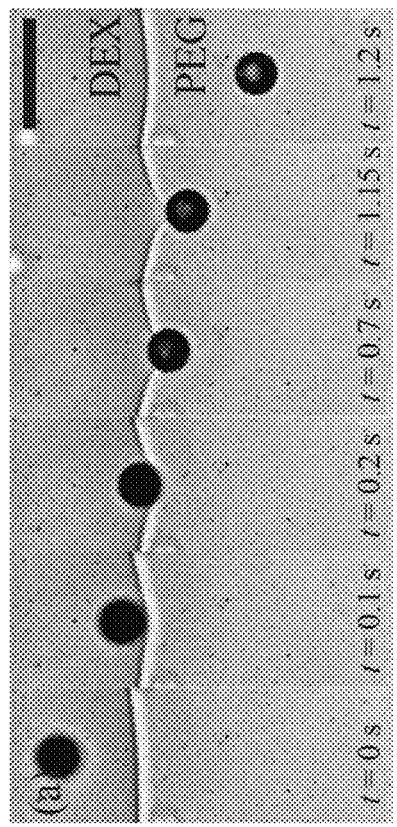
FIGS. 8A and 8B are photomicrographs of a microparticle traversing a liquid-liquid interface in accordance with the teachings herein.
Figure 8B:
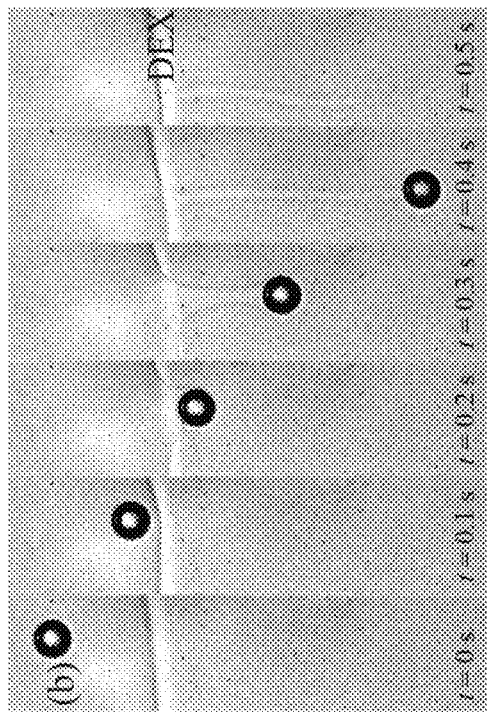

Referring now to FIGS. 8A and 8B, shown therein are instances, at the micrometer scale, in which a self-assembled particle may be non-coated or coated as it traverses the liquid-liquid interface, depending on the value of the magnetic Bond number $Bo_m$. The time-lapse image panels of FIG. 8A illustrate the traversal of a particle across a liquid-liquid interface (in which the particle is not becoming coated during the traversal) under a small magnetic Bond number $Bo_m \approx 0.3$ and an interfacial tension of $\gamma \approx 0.150$ mN/m. At the panel in FIG. 8A labeled "t=0.2 s", a DEX fluid film between the particle and the liquid-liquid interface may completely drain away, where the three-phase contact line between the DEX phase, the PEG phase and the solid phase of the particle may be formed and the particle appears to "snap-in" with the ATPS interface. The particle may subsequently detach from the interface at the panel of FIG. 8A labeled "t=0.15 s", and pass into the PEG phase. This type of particle traversal may be analogous to the drainage regime as described in classical fluid mechanics literature, and the "snap-in" behavior may also be observed under co-laminar flow geometries. In some cases, where $Bo_m \ll 1$, the film drainage process may be gradual. In other cases, the particle may become adsorbed into the liquid-liquid interface, remain on the interface and become washed into one of the side channels along with the moving fluid.

The image panels shown in FIG. 8B illustrate the traversal of a particle across a liquid-liquid interface under a relatively larger magnetic Bond number $Bo_m \approx 3$ and an interfacial tension of $\gamma \approx 0.012$ mN/m and the particle is being coated as it traverses the liquid-liquid interface. In this case, the magnetic force overcomes the interfacial tension restoring force from the liquid-liquid interface and the particle may pass from the DEX phase into the PEG phase without becoming adsorbed into the liquid-liquid interface. Particles that successfully traverse the liquid-liquid interface in this manner may entrain a thin film (i.e. become coated) with the DEX phase as they pass through the interface. The entrained DEX phase may form an interfacial tail behind the particle as the particle moves further into the PEG phase. Particle clusters that traverse the liquid-liquid interface in a high magnetic Bond number regime (i.e. $Bo_m \gg 1$) may similarly entrain a thin coating film of the DEX phase as they pass into the PEG phase.

Figure 9:
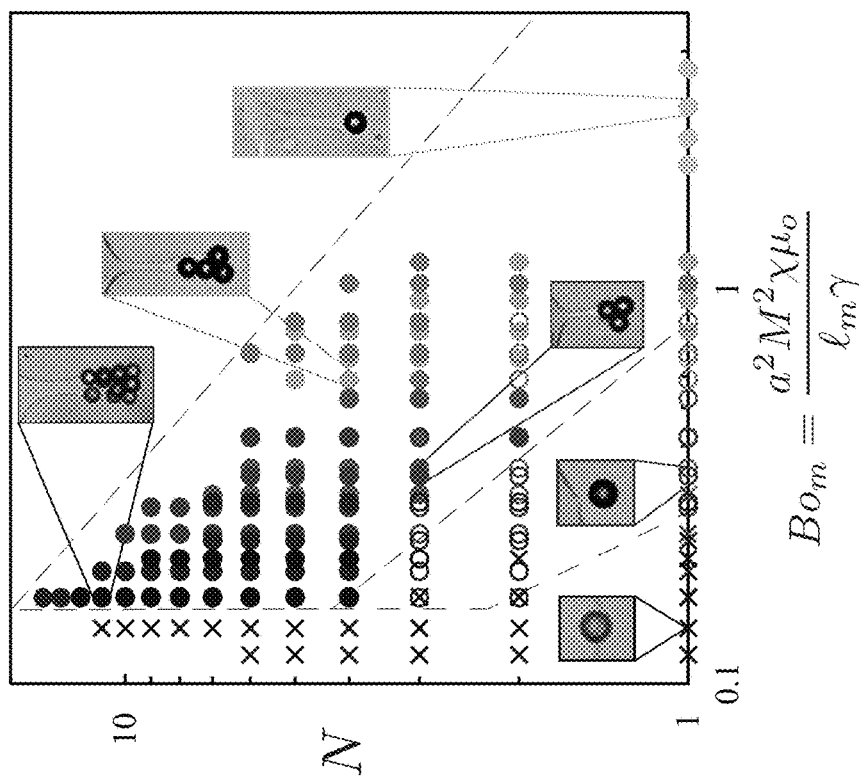
FIG. 9 is a regime map illustrating fluid entrainment by particle cluster size as a function of magnetic Bond number in accordance with the teachings herein.

Referring now to FIG. 9, shown therein is an example regime map illustrating fluid entrainment characteristics by particle cluster size N as a function of magnetic Bond number $Bo_m$. As noted previously, the magnetic Bond number $Bo_m$ takes into consideration the interfacial tension at the interface between two liquid phases. As such, the trends observed in FIG. 9 may be generalized for other liquid-liquid interfaces, and is not restricted to DEX-PEG interfaces. The solid circles in FIG. 9 represent traversals in the tailing regime, where particles and/or clusters may pass through the ATPS liquid-liquid interface and entrain a thin film of the DEX phase. The open circles represent traversals in the drainage regime, where all of the DEX phase may drain away prior to the particles and/or clusters passing through the ATPS liquid-liquid interface. The crosses represent instances where particles and clusters may not be able to pass through the ATPS liquid-liquid interface. The plot indicates that generally, particles or clusters of a given size N may be coated under conditions where $Bo_m \gg 1$ while particles or clusters a given size N may less likely be coated when $Bo_m \ll 1$.

It should be noted that a change in polymer or a change in polymer concentration in at least one of the two liquids may change the interfacial tension. Since the interfacial tension is one of the terms in the magnetic Bond number this may have an effect on whether a particle or aggregation of parties is coated or not when traversing the liquid-liquid interface. For example, if one reduces the PEG concentration, the interfacial tension is lowered which raises the magnetic Bond number.

For single particles, if the magnetic Bond number $Bo_m$ is greater than unity (i.e. magnetic forces dominate interfacial restoration), particles may traverse the liquid-liquid interface without forming a three-phase contact line, and move into the PEG phase while retaining a coating layer of DEX. As the particles continue into the PEG phase, the interfacial tail behind the particle may become thinner and eventually rupture. As the magnetic Bond number $Bo_m$ is reduced to approximately unity, particles that reach the interface may become adsorbed onto the interface and form the three-phase contact line. These particles may be able to detach from the interface to pass into the PEG phase, but do not become coated with a film of the DEX phase.

Similar observations for particle clusters may be made. When the magnetic Bond number $Bo_m$ is large, particle clusters may traverse the liquid-liquid interface in the tailing regime, and entrain a thin film of the DEX phase. At lower values of magnetic Bond number $Bo_m$, the clusters may approach the liquid-liquid interface in the drainage regime, and the DEX fluid layer completely drains away before the particle clusters pass through the interface. However, the transition between the tailing and drainage regimes may occur at a lower magnetic Bond number $Bo_m$, for particle clusters, in comparison to individual particles.

Figure 10A:
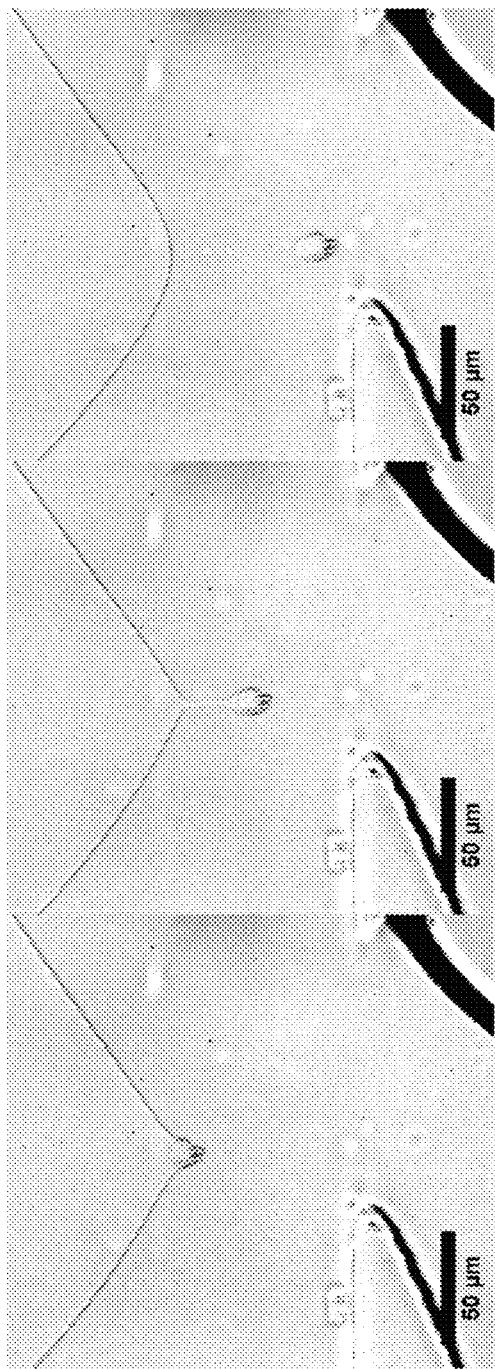
FIGS. 10A and 10B are photomicrographs of magnetized cells traversing a liquid-liquid interface in accordance with the teachings herein.
Figure 10B:

For example, it has been found in experiments using DEX and PEG as example fluid phases, as shown in FIGS. 10A and 10B, that as long as the DEX-PEG viscosity ratio and the magnetic Bond number are both greater than unity then a thin coating film will be formed on the surface of the magnetized cell. Specifically, FIGS. 10A and 10B each depict a time-series photomicrograph (progressing from left to right) of magnetized cells traversing the liquid-liquid interface. FIG. 10A shows a single magnetized cell being coated as it passes through the DEX-PEG interface. FIG.

10B shows a cluster of more than 10 cells being coated as it travels through the DEX-PEG interface. The number of cells coated in a single coating of film may be adjusted by varying the magnetic Bond number which is tied to various experimental parameters, namely, the interfacial tension and the magnetic field strength, as well as polymer concentrations as explained previously.

The coated particle clusters may coalesce with other coated particle clusters upon contact with each other in the collection reservoir 260 (see e.g. FIG. 2). Likewise, the coated single particles may coalesce with other coated particles upon contact with each other in the collection reservoir 260. Accordingly, this method of coating particles may be particularly well suited to generating coated cell clusters using magnetically tagged cells. This may be used in various applications including, but not limited to, immunoisolating cells for cell transplantation operations, for example. The ability to control the size of the coated cluster, in an all-biocompatible ATPS environment may be desirable in this and other biomedical applications.

However, achieving useful cell clustering and coating may require the implementation of a polymerization scheme that solidifies the coating film. In some embodiments, a polymerizable compound such as, but not limited to, alginate, for example, may be introduced into the first liquid phase (e.g. the DEX phase) along with the cells and/or particles. These components may then flow to the liquid-liquid interface, self-assemble, and traverse the interface. Under some conditions, as described above, the particles or clusters may be coated and arrive in the collection chamber 260. To enable polymerization of the polymerizable compound, a polymerization agent may be introduced to the second liquid phase (e.g. the PEG phase) since the polymerization agent is required to react with the polymer in the coating phase to polymerize. For example, in the case of alginate, calcium chloride may be used and introduced to the PEG phase. In some implementations 1-40 wt % alginate and 1-30 wt % calcium chloride may be used, for example, and other concentrations are possible. Some of the calcium chloride may diffuse into the DEX phase that encapsulates the particles or cells to polymerize the alginate, as the particles or cells travel to the collection chamber 260.

In other embodiments, the polymerizable compound that is used may be photo-sensitive such that the polymerization process is triggered upon exposure to light of a specific wavelength such as ultraviolet light, for example. As an example, Polyethylene (glycol) Diacrylate (PEG-DA) may be combined with a photoinitiator such that the combination may be polymerized with UV light. The aqueous PEG-DA mixtures may comprise from 1-40 vol % PEG-DA and 0.1-10 vol % photoinitiator, for example, although other concentrations are possible. The polymerizable compound may be introduced in a similar manner described above. After the cells and/or particles traverse across the liquid-liquid interface and become coated with the polymerizable compound, the aggregates may then be exposed to the light source.

It should be noted that the magnetic force on a magnetically tagged cell will be equal to the magnetic force acting on all of the paramagnetic particles that are attached to the cell surface. Generally cells (unless they are somehow loaded with iron) have negligible paramagnetism but when paramagnetic particles are attached to the cells, the cell-particle system becomes paramagnetic because of the presence of the particles (while the cells themselves remain non-magnetic). Since magnetic force is a volume force, the total magnetic force on a magnetically tagged cell will be proportional to the combined volume of all of the particles attached to the cell. The other relevant forces acting on the cell are: (1) the viscous drag from the surrounding fluid and (2) the restorative force due to interfacial tension for cells that are near or at the liquid-liquid interface. The viscous drag force is proportional to an object's size (for example, the cell's radius), and the restorative force from interfacial tension is also proportional to an object's size (i.e. cell radius). Therefore, as a given cell gets larger, the number of paramagnetic particles that have to be attached to the given cell's surface may increase with the square of the cell's radius (since the surface area of the cell increases with the square of the cell's surface). Therefore, larger cells may be more sensitive to magnetic forcing because the increase in drag and interfacial tension force (which scales with radius to the power of 1) may be less significant than the increase in the total magnetic force (which scales with the radius to the power of 2). However, compared to particles, a stronger magnetic force (e.g. from a shorter distance between the magnet and the ATPS liquid-liquid interface) is likely needed to get the cells to pass through the ATPS liquid-liquid interface since the net magnetic force on a cell-particle system will be lower than the net magnetic force on a single particle or a cluster of particles, on a volume basis, because the volume occupied by the cell will essentially be non-magnetic.

In some embodiments, the efficiency of the particle cluster formation and coating technique (including the application to cells) can be improved by providing additional serial flow focusing junctions, so that particles enter the crossflow chamber in approximately a straight line, and all reach the apex (i.e. stagnation point) of the liquid-liquid interface. For example, the microfluidic system 100 of FIG. 1A may be modified to have more inlets for the first liquid (e.g. DEX phase) so the particles may be more "flow focused" towards the center of the corresponding microchannels and arrive at the center of the liquid-liquid interface where the flow is stagnant. The slower flow may facilitate the traversal of more particle clusters through the interface instead of being driven to the side flows that exit through the side outlets. In an alternative embodiment, the microfluidic system may be maintained with two inlets for the first liquid (DEX phase) but the flow rate corresponding to the phase sheath flow may be increased, for example, by adjusting the operating parameters of the syringe pumps connected to the outer sheath flow inlet (e.g. inlet 110 of FIG. 1) to increase the flow rate to result in "flow focus" of particles to the center of the corresponding microchannels.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A microfluidic device for processing at least one sample particle that is paramagnetic, the device comprising:
   a cross-slot chamber including:
      an upper inlet portion that receives a first fluid during use, the first fluid containing the at least one sample particle;
      a lower inlet portion disposed below the upper inlet portion that receives a second fluid during use;

third and fourth side outlet portions disposed on either of the cross-slot chamber between the upper and lower inlet portions, for providing symmetrical outlets for the first and second fluids during use; and a collection chamber for collecting the processed at least one sample particle; and a magnetic field source for providing a magnetic field that encompasses at least a portion of the cross-slot chamber, wherein, during use the first fluid is introduced along a first axis into the cross-slot chamber and the second fluid is introduced along a second axis into the cross-slot chamber, the second axis being transverse to the first axis, the first and second fluids being aqueous and immiscible with respect to one another to create first and second fluid phases with a liquid-liquid interface providing an interfacial tension therebetween in the cross-slot chamber, and the magnetic field encompasses the liquid-liquid interface and is adjustable to impart a magnetic force to control movement of the at least one sample particle across the liquid-liquid interface in the cross-slot chamber.

2. The device of claim 1, wherein the liquid-liquid interface is non-linear and comprises at least one apex, the liquid-liquid interface and the at least one apex being in the cross-slot chamber, and during use the flows of the first and second fluids produce an extensional flow field with at least one stagnation point at the at least one apex.

3. The device of claim 2, wherein the magnetic field strength is adjustable for pulling the at least one particle across the liquid-liquid interface where the at least one particle is coated with a layer of liquid from the first fluid.

4. The device of claim 2, wherein at least two sample particles that are paramagnetic are brought to the liquid-liquid interface and assembled into a particle cluster due to at least one of the magnetic field and the interfacial tension.

5. The device of claim 2, wherein at least two sample particles that are paramagnetic are brought to the liquid-liquid interface and assembled into at least two sample particle chains due to at least one of the magnetic field strength and the interfacial tension.

6. The device of claim 4, wherein the magnetic field strength is adjustable for pulling the at least two sample particles across the liquid-liquid interface where the at least two sample particles are coated with a layer of liquid from the first fluid.

7. The device of claim 5, wherein the at least two sample particle chains assemble into a cluster of sample particle chains before crossing the liquid-liquid interface.

8. The device of claim 1, wherein there are a plurality of paramagnetic particles and a cell having a cell membrane with at least one cell surface receptor, wherein the paramagnetic particles are functionalized to bond with the at least one cell surface receptor and processed to cross the liquid-liquid interface and be coated with a liquid layer from the first fluid.

9. The device of claim 1, wherein the magnetic field source is a permanent magnet that is aligned with the center of the liquid-liquid interface.

10. The device of claim 1, wherein the magnetic field source is an electromagnet that is aligned with the center of the liquid-liquid interface, and the magnetic field is varied by varying a current through the electromagnet during use.

11. The device of claim 1, wherein the first fluid and the second fluid are both aqueous polymer mixtures and the polymers are incompatible with one another.

12. The device of claim 1, wherein the device comprises:
first and second fluid inlets for receiving the first fluid during use;
first and second fluid microchannel networks having first and second input portions coupled to the first and second fluid inlets, respectively, the first fluid microchannel network having a first output portion being coupled to the second fluid microchannel network between the second fluid inlet and a second output portion of the second microchannel network, and the second output portion of the second microchannel network being coupled to the upper inlet portion of the cross-slot chamber;
a third fluid inlet for receiving the second fluid during use; and
a third microchannel network having a third input portion coupled to the third fluid inlet and a third output portion coupled to the lower inlet portion of the cross-slot chamber.

13. The device of claim 12, wherein the second output of the second microchannel network comprises a single microchannel having a first microchannel axis and the third output portion of the third microchannel comprises two microchannels with axes transverse to the first microchannel axis on either side of the lower portion of the cross-slot chamber.

14. The device of claim 12, wherein the lower inlet portion of the cross-slot chamber is wider than the upper inlet portion of the cross-slot chamber.

15. A method of processing at least one sample particle that is paramagnetic in a microfluidic device, the method comprising:
providing a cross-slot fluid chamber for the microfluidic device;
introducing the first fluid along a first axis into the cross-slot chamber and introducing the second fluid along a second axis into the cross-slot chamber, the second axis being transverse to the first axis, the first and second fluids being aqueous and immiscible with respect to one another to create first and second fluid phases with a liquid-liquid interface having an interfacial tension therebetween in the cross-slot chamber;
providing a magnetic field that encompasses the liquid-liquid interface; and
adjusting the magnetic field to impart a magnetic force to control movement of the at least one particle across the liquid-liquid interface in the cross-slot chamber.

16. The method of claim 15, wherein the method comprises providing the cross-slot fluid chamber with an upper inlet portion that receives the first fluid during use, the first fluid containing the at least one sample particle; a lower inlet portion disposed below the upper inlet portion that receives the second fluid during use; third and fourth side outlet portions disposed on either of the cross-slot chamber between the upper and lower inlet portions, for providing symmetrical outlets for the first and second fluids during use; and a collection chamber for collecting the processed at least one sample particle.

17. The method of claim 16, wherein the liquid-liquid interface is non-linear and comprises at least one apex, the liquid-liquid interface and the at least one apex being in the cross-slot chamber, and the flows of the first and second fluids produce an extensional flow field with at least one stagnation point at the at least one apex.

18. The method of claim 17, the method further comprises adjusting the magnetic field strength for pulling the at least one sample particle across the liquid-liquid interface and coating the at least one sample particle with a layer of liquid from the first fluid.

19. The method of claim 18, the method further comprises bringing at least two sample particles that are paramagnetic to the liquid-liquid interface and assembling the at least two sample particles into a particle cluster due to at least one of the magnetic field strength and the interfacial tension.

20. The method of claim 18, the method further comprises bringing at least two sample particles that are paramagnetic to the liquid-liquid interface and assembling the at least two sample particles into at least two particle chains due to at least one of the magnetic field strength and the interfacial tension.

21. The method of claim 19, wherein the method further comprises adjusting the magnetic field strength for pulling the at least two sample particles across the liquid-liquid interface and coating the at least two particles with a layer of liquid from the first fluid.

22. The method of claim 20, the method further comprises assembling the at least two sample particle chains into a cluster of sample particle chains before crossing the liquid-liquid interface.

23. The method of claim 15, wherein there are a plurality of paramagnetic particles and a cell having a cell membrane with at least one cell surface receptor, and the method further comprises functionalizing the paramagnetic particles to bond with the at least one cell surface receptor and processing the cell and paramagnetic particles for crossing the liquid-liquid interface and being coated with a liquid layer from the first fluid.

24. The method of claim 15, wherein the magnetic field source is a permanent magnet, and the method further comprises aligning the permanent magnet with the center of the liquid-liquid interface and adjusting the distance of the permanent magnet with respect to the cross-slot chamber to provide a desired magnetic field strength.

25. The method of claim 15, wherein the magnetic field source is an electromagnet, and the method further comprises aligning the electromagnet with the center of the liquid-liquid interface, and adjusting the magnetic field by varying a current through the electromagnet during use.

26. The method of claim 15, wherein the first fluid and the second fluids are both aqueous polymer mixtures and the polymers are incompatible with one another.

* * * * *

UNITED STATES PATENT AND TRADEMARK OFFICE
CERTIFICATE OF CORRECTION

PATENT NO. : 10,124,337 B2
APPLICATION NO. : 15/424048
DATED : November 13, 2018
INVENTOR(S) : Scott Tsai, Steven Jones and Eric Jervis Page 1 of 1

It is certified that error appears in the above-identified patent and that said Letters Patent is hereby corrected as shown below:

On the Title Page

Item (71), the Applicants, "Scott Tsai, Newmarket (CA); Steven Jones, Newmarket (CA); Eric Jervis, Vancouver (CA)" should read -- Scott Tsai, Newmarket (CA); Steven Jones, Newmarket (CA); STEMCELL Technologies Canada Inc., Vancouver (CA) --.

Signed and Sealed this
Third Day of November, 2020

Andrei Iancu
*Director of the United States Patent and Trademark Office*